US012565499B2

(12) United States Patent
Mates et al.

(10) Patent No.: US 12,565,499 B2
(45) **Date of Patent: *Mar. 3, 2026**

(54) COMPOUNDS AND METHODS

(71) Applicant: INTRA-CELLULAR THERAPIES, INC., New York, NY (US)

(72) Inventors: Sharon Mates, New York, NY (US); Robert Davis, San Diego, CA (US); Kimberly Vanover, New York, NY (US); Lawrence Wennogle, Hillsborough, NJ (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/601,923

(22) Filed: Mar. 11, 2024

(65) Prior Publication Data

US 2024/0208974 A1 Jun. 27, 2024

Related U.S. Application Data

(63) Continuation of application No. 17/405,736, filed on Aug. 18, 2021, now Pat. No. 11,958,852, which is a continuation of application No. 16/585,251, filed on Sep. 27, 2019, now Pat. No. 11,124,514, which is a continuation of application No. 14/394,470, filed as application No. PCT/US2013/036515 on Apr. 14, 2013, now abandoned.

(60) Provisional application No. 61/671,723, filed on Jul. 14, 2012, provisional application No. 61/671,713, filed on Jul. 14, 2012, provisional application No. 61/624,293, filed on Apr. 14, 2012, provisional application No. 61/624,292, filed on Apr. 14, 2012, provisional application No. 61/624,291, filed on Apr. 14, 2012.

(51) Int. Cl.

| | |
|---|---|
| ***C07D 471/14*** | (2006.01) |
| ***A61K 31/445*** | (2006.01) |
| ***A61K 31/4985*** | (2006.01) |
| ***A61K 31/5383*** | (2006.01) |
| ***A61K 45/06*** | (2006.01) |
| ***A61P 25/28*** | (2006.01) |
| ***C07D 471/16*** | (2006.01) |

(52) U.S. Cl.

CPC .......... *C07D 471/14* (2013.01); *A61K 31/445* (2013.01); *A61K 31/4985* (2013.01); *A61K 31/5383* (2013.01); *A61K 45/06* (2013.01); *A61P 25/28* (2018.01); *C07D 471/16* (2013.01)

(58) Field of Classification Search

CPC .............. A61K 2300/00; A61K 31/445; A61K 31/4985; A61K 31/5383; A61K 45/06; A61P 21/02; A61P 25/00; A61P 25/06; A61P 25/14; A61P 25/16; A61P 25/18; A61P 25/20; A61P 25/22; A61P 25/24; A61P 25/28; A61P 3/04; A61P 31/00; A61P 43/00; C07D 471/14; C07D 471/16

See application file for complete search history.

(56) References Cited

U.S. PATENT DOCUMENTS

| | | | |
|---|---|---|---|
| 2,490,813 | A | 12/1949 | Hughes et al. |
| 3,299,078 | A | 1/1967 | Pachter et al. |
| 3,813,392 | A | 5/1974 | Sellsdet et al. |
| 3,914,421 | A | 10/1975 | Rajagopala |
| 4,001,263 | A | 1/1977 | Plattner et al. |
| 4,115,577 | A | 9/1978 | Rajagopala |
| 4,183,936 | A | 1/1980 | Rajagopala |
| 4,219,550 | A | 8/1980 | Rajagopala |
| 4,238,607 | A | 12/1980 | Rajagopala |
| 4,389,330 | A | 6/1983 | Tice et al. |
| 4,522,944 | A | 6/1985 | Doria et al. |
| 4,530,840 | A | 7/1985 | Tice et al. |
| 4,971,971 | A | 11/1990 | Tokunaga et al. |
| 4,985,432 | A | 1/1991 | Tokunaga et al. |
| 5,114,976 | A | 5/1992 | Norden |
| 5,538,739 | A | 7/1996 | Bodmer et al. |
| 5,576,460 | A | 11/1996 | Buchwald et al. |
| 5,648,539 | A | 7/1997 | Goodbrand et al. |
| 5,648,542 | A | 7/1997 | Goodbrand et al. |
| 5,654,482 | A | 8/1997 | Goodbrand et al. |
| 5,705,697 | A | 1/1998 | Goodbrand et al. |
| 5,723,669 | A | 3/1998 | Goodbrand et al. |

(Continued)

FOREIGN PATENT DOCUMENTS

| | | |
|---|---|---|
| EP | 0 058 481 | 8/1982 |
| EP | 0 856 508 | 8/1998 |

(Continued)

OTHER PUBLICATIONS

Castaneda et al. (Journal of Affective Disorders 106 (2008) 1-27) (Year: 2008).*
Bora et al. (Schizophrenia Bulletin vol. 36 No. 1 pp. 112-125, 2010). (Year: 2010).*
Avendano et al., "The problem of the existence of C(Ar)—H . . . N Intramolecular Hydrogen Bonds in a Family of 9-Azaphenyl-9H-carbazoles," J. Chem. Soc. Perkin Trans., vol. 2, p. 1547-1555, (1993).
Balbach et al. "Pharmaceutical evaluation of early development candidates the 100 mg-approach", International Journal of Pharmaceutics, vol. 275, p. 1-12 (2004).

(Continued)

*Primary Examiner* — Umamaheswari Ramachandran
(74) *Attorney, Agent, or Firm* — Hoxie & Associates LLC

(57) ABSTRACT

The present invention relates to use of particular substituted heterocycle fused gamma-carbolines as described herein, in free, pharmaceutically acceptable salt or prodrug form, and pharmaceutical composition comprising the same optionally in combination with one or more agents, for the prophylaxis or treatment of one or more disorders associated with dementia, particularly behavioral or mood disturbances (e.g., agitation/aggression), psychosis, depression and sleep disturbances among others in patients suffering from dementia.

13 Claims, No Drawings

(56) References Cited

U.S. PATENT DOCUMENTS

| | | | |
|---|---|---|---|
| 5,723,671 | A | 3/1998 | Goodbrand et al. |
| 5,847,166 | A | 12/1998 | Buchwald et al. |
| 5,902,901 | A | 5/1999 | Goodbrand et al. |
| 6,043,370 | A | 3/2000 | Kubo et al. |
| 6,166,226 | A | 12/2000 | Buchwald et al. |
| 6,235,936 | B1 | 5/2001 | Buchwald et al. |
| 6,307,087 | B1 | 10/2001 | Buchwald et al. |
| 6,323,366 | B1 | 11/2001 | Wolfe et al. |
| 6,395,916 | B1 | 5/2002 | Buchwald et al. |
| 6,407,092 | B1 | 6/2002 | Hester et al. |
| 6,465,693 | B2 | 10/2002 | Buchwald et al. |
| 6,541,639 | B2 | 4/2003 | Zhou et al. |
| 6,548,493 | B1 | 4/2003 | Robichaud et al. |
| 6,552,017 | B1 | 4/2003 | Robichaud et al. |
| 6,699,852 | B2 | 3/2004 | Robichaud et al. |
| 6,713,471 | B1 | 3/2004 | Robichaud et al. |
| 6,759,554 | B2 | 7/2004 | Buchwald et al. |
| 6,762,329 | B2 | 7/2004 | Marcoux et al. |
| 6,849,619 | B2 | 2/2005 | Robichaud et al. |
| 6,867,298 | B2 | 3/2005 | Buchwald et al. |
| 6,888,032 | B2 | 5/2005 | Buchwald et al. |
| 6,946,560 | B2 | 9/2005 | Buchwald et al. |
| 7,026,498 | B2 | 4/2006 | Buchwald et al. |
| 7,071,186 | B2 | 7/2006 | Robichaud et al. |
| 7,081,455 | B2 | 7/2006 | Robichaud et al. |
| 7,109,339 | B2 | 9/2006 | Lee et al. |
| 7,115,784 | B2 | 10/2006 | Buchwald et al. |
| 7,183,282 | B2 | 2/2007 | Robichaud et al. |
| 7,223,879 | B2 | 5/2007 | Buchwald et al. |
| RE39,679 | E | 6/2007 | Robichaud et al. |
| RE39,680 | E | 6/2007 | Robichaud et al. |
| 7,238,690 | B2 | 7/2007 | Robichaud et al. |
| 7,247,731 | B2 | 7/2007 | Buchwald et al. |
| 7,323,608 | B2 | 1/2008 | Buchwald et al. |
| 7,375,226 | B2 | 5/2008 | Jolidon et al. |
| 7,462,641 | B2 | 12/2008 | Igo et al. |
| 7,592,454 | B2 | 9/2009 | Lee et al. |
| 7,601,740 | B2 | 10/2009 | Weiner et al. |
| 8,309,722 | B2 | 11/2012 | Tomesch et al. |
| 8,309,772 | B2 | 11/2012 | Weiner et al. |
| 8,598,119 | B2 | 12/2013 | Mates et al. |
| 8,648,077 | B2 | 2/2014 | Tomesch et al. |
| 8,779,139 | B2 | 7/2014 | Tomesch et al. |
| 8,791,138 | B2 | 7/2014 | Seeman et al. |
| 8,993,572 | B2 | 3/2015 | Mates et al. |
| 9,168,258 | B2 | 10/2015 | Mates et al. |
| 9,199,995 | B2 | 12/2015 | Tomesch et al. |
| 9,315,504 | B2 | 4/2016 | Tomesch et al. |
| 9,371,324 | B2 | 6/2016 | Mates et al. |
| 9,428,506 | B2 | 8/2016 | Mates et al. |
| 9,586,960 | B2 | 3/2017 | Tomesch et al. |
| 9,616,061 | B2 | 4/2017 | Mates et al. |
| 9,708,322 | B2 | 7/2017 | Li et al. |
| 9,745,300 | B2 | 8/2017 | Mates et al. |
| 9,751,883 | B2 | 9/2017 | Tomesch et al. |
| 9,956,227 | B2 | 5/2018 | Vanover et al. |
| 10,072,010 | B2 | 9/2018 | Li et al. |
| 10,077,267 | B2 | 9/2018 | Mates et al. |
| 10,117,867 | B2 | 11/2018 | Mates et al. |
| 10,245,260 | B2 | 4/2019 | Yao et al. |
| 10,322,134 | B2 | 6/2019 | Vanover et al. |
| 10,464,938 | B2 | 11/2019 | Tomesch et al. |
| 10,472,359 | B2 | 11/2019 | Li et al. |
| 10,597,394 | B2 | 3/2020 | Mates et al. |
| 10,654,854 | B2 | 5/2020 | Li et al. |
| 10,688,097 | B2 | 6/2020 | Yao et al. |
| 10,695,345 | B2 | 6/2020 | Li et al. |
| 10,702,522 | B2 | 7/2020 | Mates et al. |
| 10,716,786 | B2 | 7/2020 | Li et al. |
| 10,799,500 | B2 | 10/2020 | Yao et al. |
| 10,844,061 | B2 | 11/2020 | Li et al. |
| 10,899,762 | B2 | 1/2021 | Mates et al. |
| 10,960,009 | B2 | 3/2021 | Vanover et al. |
| 10,960,010 | B2 | 3/2021 | Vanover et al. |
| 11,014,925 | B2 | 5/2021 | Li et al. |
| 11,026,951 | B2 | 6/2021 | Mates et al. |
| 11,052,083 | B2 | 7/2021 | Li et al. |
| 11,052,084 | B2 | 7/2021 | Li et al. |
| 11,053,245 | B2 | 7/2021 | Mates et al. |
| 11,096,944 | B2 | 8/2021 | Yao et al. |
| 11,124,514 | B2 | 9/2021 | Mates et al. |
| RE48,825 | E | 11/2021 | Tomesch et al. |
| RE48,839 | E | 12/2021 | Mates et al. |
| 11,292,793 | B2 | 4/2022 | Peddy et al. |
| 11,311,536 | B2 | 4/2022 | Li et al. |
| 11,331,316 | B2 | 5/2022 | Li et al. |
| 11,376,249 | B2 | 7/2022 | Li et al. |
| 11,407,751 | B2 | 8/2022 | Tomesch et al. |
| 11,427,587 | B2 | 8/2022 | Li et al. |
| 11,440,911 | B2 | 9/2022 | Wennogle et al. |
| 11,680,065 | B2 | 6/2023 | Li et al. |
| 11,690,842 | B2 | 7/2023 | Li et al. |
| 11,753,419 | B2 | 9/2023 | Li et al. |
| 11,806,347 | B2 | 11/2023 | Li et al. |
| 11,806,348 | B2 | 11/2023 | Li et al. |
| 11,957,791 | B2 | 4/2024 | Li et al. |
| 11,958,852 | B2 | 4/2024 | Mates et al. |
| 11,980,617 | B2 | 5/2024 | Snyder et al. |
| 12,070,459 | B2 | 8/2024 | Li et al. |
| 12,090,155 | B2 | 9/2024 | Mates et al. |
| 12,122,792 | B2 | 10/2024 | Li et al. |
| 12,128,043 | B2 | 10/2024 | Li et al. |
| 12,144,808 | B2 | 11/2024 | Li et al. |
| 12,195,464 | B2 | 1/2025 | Li |
| 2001/0008942 | A1 | 7/2001 | Buchwald et al. |
| 2004/0034015 | A1 | 2/2004 | Robichaud et al. |
| 2004/0092534 | A1 | 5/2004 | Yam et al. |
| 2004/0127482 | A1 | 7/2004 | Robichaud et al. |
| 2004/0142970 | A1 | 7/2004 | Chung et al. |
| 2008/0069885 | A1 | 3/2008 | Mesens et al. |
| 2008/0132552 | A1 | 6/2008 | Kleinman et al. |
| 2008/0280941 | A1 | 11/2008 | Lourtie et al. |
| 2008/0287450 | A1 | 11/2008 | Cid-Nunez et al. |
| 2009/0202631 | A1 | 8/2009 | Yam et al. |
| 2010/0113781 | A1 | 5/2010 | Tomesch et al. |
| 2010/0298382 | A1 | 11/2010 | Seeman et al. |
| 2011/0071080 | A1 | 3/2011 | Mates et al. |
| 2011/0112105 | A1* | 5/2011 | Tomesch ................ A61P 25/24 514/250 |
| 2011/0269777 | A1 | 11/2011 | Bachurin et al. |
| 2013/0202692 | A1 | 8/2013 | Mates et al. |
| 2014/0080816 | A1 | 3/2014 | Koolman et al. |
| 2015/0072964 | A1 | 3/2015 | Mates et al. |
| 2015/0079172 | A1 | 3/2015 | Mates et al. |
| 2015/0166540 | A1 | 6/2015 | Mates et al. |
| 2015/0374684 | A1 | 12/2015 | Javitt et al. |
| 2016/0031885 | A1 | 2/2016 | Li et al. |
| 2016/0194325 | A1 | 7/2016 | Tomesch et al. |
| 2016/0194326 | A1 | 7/2016 | Tomesch et al. |
| 2016/0310502 | A1 | 10/2016 | Vanover |
| 2019/0192511 | A1 | 6/2019 | Li et al. |
| 2019/0211015 | A1 | 7/2019 | Mittelman et al. |
| 2021/0000822 | A1 | 1/2021 | Mates et al. |
| 2021/0060009 | A1 | 3/2021 | Synder et al. |
| 2021/0186962 | A1 | 6/2021 | Davis et al. |
| 2023/0372336 | A1 | 11/2023 | Dutheil et al. |
| 2024/0122924 | A1 | 4/2024 | Dutheil et al. |
| 2025/0195510 | A1 | 6/2025 | Dutheil et al. |

FOREIGN PATENT DOCUMENTS

| | | |
|---|---|---|
| EP | 0 976 732 | 2/2000 |
| EP | 1 245 553 | 10/2002 |
| EP | 1 254 884 | 11/2002 |
| EP | 1 564 671 | 1/2005 |
| EP | 1 539 115 | 6/2005 |
| GB | 1476087 | 6/1977 |
| GB | 2145422 | 3/1985 |
| WO | WO 1994/024125 | 10/1994 |
| WO | WO 1995/013814 | 5/1995 |
| WO | WO 1998/015515 | 4/1998 |
| WO | WO 1998/043956 | 10/1998 |
| WO | WO 1999/043643 | 9/1999 |
| WO | WO 2000/002887 | 1/2000 |

(56) References Cited

FOREIGN PATENT DOCUMENTS

| | | |
|---|---|---|
| WO | WO 2000/035419 | 6/2000 |
| WO | WO 2000/064899 | 11/2000 |
| WO | WO 2000/077001 | 12/2000 |
| WO | WO 2000/077002 | 12/2000 |
| WO | WO 2000/077010 | 12/2000 |
| WO | WO 2002/085838 | 10/2002 |
| WO | WO 2003/014118 | 2/2003 |
| WO | WO 2004/010981 | 2/2004 |
| WO | WO 2004/013094 | 2/2004 |
| WO | WO 2004/039788 | 5/2004 |
| WO | WO 2004/056324 | 7/2004 |
| WO | WO 2008/112280 | 9/2008 |
| WO | WO 2009/114181 | 9/2009 |
| WO | WO 2009/145900 | 12/2009 |
| WO | WO 2011/133224 | 10/2011 |
| WO | WO 2013/155504 | 10/2013 |
| WO | WO 2013/155505 | 10/2013 |
| WO | WO 2013/155506 | 10/2013 |
| WO | WO 2014/145192 | 9/2014 |
| WO | WO 2015/085004 | 6/2015 |
| WO | WO 2015/154025 | 10/2015 |
| WO | WO 2015/154030 | 10/2015 |
| WO | WO 2015/191554 | 12/2015 |

OTHER PUBLICATIONS

Barman et al., "Newer Antipsychotics: Brexpiprazole, Cariprazine, and Lumateperone: A Pledge or Another Unkept Promise?," World J. Psychiatr., vol. 11, No. 12, p. 1228-1238, (2021).

Bastin et al, "Salt Selection and Optimized Procedures for Pharmaceutical New Chemical Entities", Organic Process and Research Development, vol. 4, No. 5, p. 427-435 (2000).

Bechtold et al., "Circadian Dysfunction in Disease," *Trends in Pharmacological Sciences*, vol. 31, No. 5, pp. 191-197, (2010); Abstract Only.

Beletskaya et al., "Pd- and Cu-catalyzed selective arylation of benzotriazole," Tetrahedron Letters, vol. 39, p. 5617-5620, (1998).

Berger et al.,"Synthesis of some conformationally restricted analogs of fentanyl," Journal of Medicinal Chemistry, vol. 20, No. 4, p. 600-602. (1977).

Boger et al., "Inverse Electron Demand Diels-Alder Reactions of Heterocyclic Aza Dienes. Studies on the Toal Sybthesis of Lavendamycin . . . " J. Org. Chem., vol. 50, p. 5782-5789, (1985).

Bowman et al., "Synthesis of 1H-quinazoline-4-ones using intramolecular aromatic nucelophilic substitution," Arkivoc, vol. x, p. 434-442 (2003).

Bowman et al., "Intramolecular Aromatic Substitution (SRN1) Reactions—Use of Entrainment for the Preparation of Benzothiazoles," Tetrahedron Letters, vol. 23, p. 5093-5096, (1982).

Bowman et al., "Copper (1) Catalysed Aromatic Nuclepphilic Substitution: A Mechanistic and Synthetic Comparison with the $S_{RN}$ 1 Reaction", Tetrahedron Letters, vol. 25, No. 50, p. 5821-5824, (1984).

Bryan-Lluka et al., "Potencies of haloperidol metabolites as inhibitors of the human noradrenaline, dopamine and serotonin transporters in transfected COS-7 cells", Naunyn-Shemiedeberg's Arch Pharmacol, vol. 360, p. 109-115 (1999).

Byrn et al., "Pharmaceutical Solids: A Strategic Approach to Regulatory Considerations", Pharmaceutical Research, vol. 12, No. 7, p. 945-954 (1995).

Caira et al., "Crystalline Polymorphism of Organic Compounds", Topics in Current Chemistry, vol. 198, p. 163-203, (1998).

Calabrese et al., "Efficacy and Safety of Lumateperone for Major Depressive Episodes Associated with Bipolar I or Bipolar II Disorder: A Phase 3 Randomized Placebo-Controlled Trial," Am J Psychiatry, vol. 178, No. 12, p. 1098-1106, (2021).

Correll et al., "Efficacy and Safety of Lumateperone for Treatment of Schizophrenia: A Randomized Clinical Trial," JAMA Psychiatry, vol. 77, No. 4, p. 349-358 (2020).

Coyle et al., "Beyond the Dopamine Receptor: Novel Therapeutic Targets for Treating Schizophrenia," Dialogues Clin. Neurosci., vol. 12, No. 3, p. 359-382 (2010).

Crawford et al., "Copper-Catalyzed amidations of bromo substitutes furnas and thiophenes", Tetrahedron Letters, vol. 43, p. 7365-7368, (2002).

Davis, et al., "ITI-007 Demonstrates Brain Occupancy at Serotonin 5-$HT_{2A}$ and Dopamine $D_2$ Receptors and Serotonin Transporters Using Positron Emission Tomography in Healthy Volunteers," Psychopharmacology, vol. 232, p. 2863-2872, (2015).

Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary P93).

Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).

Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).

Edinoff et al., "Lumateperone for the Treatment of Schizophrenia," Psychopharmacology Bulletin, vol. 50, No. 4, p. 32-59 (2020).

Evindar et al., "Copper- and Palladium-Catalyzed Intramolecular Aryl Guanidinylation: An Efficient Methods for the Synthesis of a-Aminobenzimidazoles", Organic Letters, vol. 5, No. 2, p. 133-136, (2003).

Ezquerra et al., "Efficient Reagents for the Synthesis of 5-, 7-, and 5, 7-Substitues Indoles Starting from Aromatic Amines: Scope and Limitations", J. Org. Chem., vol. 61, p. 5804-5812, (1996).

Fawcett et al., "Posttraumatic Stress Disorder, Stress, and Happiness", Psychiatric Annals Journal, vol. 28, Issue 8, p. 427-428, (1998).

Fee et al., "Copper (II)-promoted solvolyses of nickel (II) complexes III. Tetradentate Schiff base ligands containing various diamine segments," Aust. J. Chem., vol. 26, p. 1475-1485, (1973).

Ferreira et al., "Novel synthetic routes to thienocarbazoles via palladium or copper catalyzed amination or amidation of arylhalides and intramolecular cyclization", Tetrahedron, vol. 58, p. 7943-7949, (2002).

Finet et al., "Recent advances in ullmann reaction: copper (II) diacetate catalysed N-, )- and S-arylation involving polycoordinate heteroatomic derivatives," Current Organic Chemistry, vol. 6, p. 597-626, (2002).

Foster et al., "Acetylcholinesterase inhibitors reduce spreading activation in dementia," Neuropsychologia, vol. 50, p. 2093-2099, (2012).

Friedman et al., "Current and Future Drug Treatment for Posttraumatic Stress Disorder Patients", Psychiatric Annals Journal, vol. 28, Issue 8, p. 464-468, (1998).

Grant et al., "Polymorphism in Pharmaceutical Solids", Chapter 1, p. 1-10 (1999).

Goodbrand et al., "Ligand-Accelerated catalysis of the Ullmann condensation: Application to hole conducting triarylamines," J. Org. Chem., vol. 64, p. 670-674, (1999).

Guillory et al., "Generation of Polymorphs, hydrates, solvates and Amorphous solids", Chapter 5, p. 183-226 (1999).

Hamann et al., Systematic Variation of Bidentate Ligands used in Aryl Halide Amination. Unexpected Effects of Steric, Electronic, and Geometric Perturbations, J. Am. Chem. Soc. vol. 120, p. 3694-3703, (1998).

Hackam et al., "Translations of Research Evidence from Animals to Humas", JAMA, vol. 296, No. 14, p. 1731-1732 (2006).

Harbert et al., "Neuroleptic Activity in 5-Aryltetrahydro-y-carbolines", J. Med. Chem., vol. 23, p. 635-643 (1980).

Harvey et al., "Serotonin and Stress: Protective or Malevolent Actions in the Biobehavioral Response to Repeated Trauma?" Annals of the New York Academy of Sciences, vol. 1032, p. 267-272; doi: 10.1196/annals.1314.035 (2004).

(56) References Cited

OTHER PUBLICATIONS

Hartwig et al., "Palladium-catalyzed amination of aryl halides: Mechanism and rational catalyst design," Synlett, p. 329-340, (1996).
Hassan et al., "Aryl-aryl bond formation one century after the discovery of the ullmann reaction," Chem. Rev., vol. 102, p. 1359-1469, (2002).
Haynes et al., "Occurrence of Pharmaceutically Acceptable Anions and Cations in the Cambridge Database", Journal of Pharmaceutical Sciences, vol. 94, No. 10, p. 2111-2120 (2005).
Herrmann et al."Memantine in dementia: A review of the current evidence," Expert Opinion on Pharmacotherapy, 2011, 12:5, 787-800 (2011).
Howes et al., "Glutamate and Dopamine in Schizophrenia: An Update for the 21st Century," J. Psychopharmacol., vol. 29, No. 2, p. 97-115 (2015).
International Search Report issued in International Application No. PCT/US2008/003340, mailed Aug. 8, 2008, 3 pages.
International Search Report issued in International Application No. PCT/US2009/001608, mailed Apr. 27, 2009, 3 pages.
International Search Report issued in International Application No. PCT/US2011/00719, mailed Jul. 5, 2011, 3 pages.
International Search Report issued in International Application No. PCT/US2013/036515, mailed Aug. 13, 2013, 3 pages.
International Search Report issued in International Application No. PCT/US2013/036514, mailed Aug. 16, 2013, 3 pages.
International Search Report issued in International Application No. PCT/US2013/036512, mailed Aug. 19, 2013, 4 pages.
Intra-Cellular Therapies, Inc., "Corporate Presentation" (Sep. 24, 2019), downloaded from https://ir.intracellulartherapies.com/static-files/93b08960-f01c-4864-aa22-8cadb3539753 (last accessed Mar. 13, 2023).
Ito et al., "Studies of organic catalytic reactions. VI. The function of pyridine and copper in the Rosenmund-von Braun reaction," Bulletin of the Chemical Society of Japan vol. 41, p. 419-423, (1968).
Izrayelit et al., "Schizoaffective Disorder and PTSD Successfully Treated With Olanzapine and Supportive Psychotherapy", Psychiatric Annals Journal, vol. 28, Issue 8, p. 424-426, (1998).
Jain et al., "Polymorphism in Pharmacy", Indian Drugs, vol. 23, No. 6, p. 315-316 (1986).
Ji et al., "Selective amination of polyhalopyridines catalyzed by a palladium-xantphos complex," Organic Letters, vol. 5, No. 24, p. 4611-4614, (2003).
Johnson, et al., "Serotonin receptor activity is necessary for olfactory learning and memory in *Drosphila melanogaster*," Neuroscience, 192:372-381 (2011).
Jordan et al., "Tamoxifen: A Most Unlikely Pioneering Medicine", Nature Reviews: Drug Discovery, vol. 2, p. 205-213, (2003).
Kametani et al., "A Novel Synthesis of Indole Derivatives", Heterocycles, vol. 14, No. 3, p. 277-280, (1980).
Kang et al., "Copper-catalyzed N-arylation of aryl iodides with benzamides or nitrogen heterocycles in the presence of ethylendiamine," Synlett, No. 3, p. 427-430, (2002).
Kendrick, "The Newer, 'Atypical' Antipsychotic Drugs—Their Development and Current Therapeutic Use," British J. General Practice, vol. 49, p. 745-749 (1999).
Kessler et al., "Lifetime Prevalence and Age-of-Onset Distributions of DSM-IV Disorders in the National Comorbidity Survey Replication", Arch Gen Psychiatry; vol. 62, p. 593-602, (2005).
Khorana et al., "Gamma-Carbolines: Binding at 5-HT5A Serotonin Receptors", Bioorganic & Medicinal Chemistry, vol. 11, Issue 5, 6, p. 717-722, p. 718 Table 1, (2003).
Kiyomori et al., "An efficient copper-catalyzed coupling of aryl halides with imidazoles," Tetrahedron Letters, vol. 40, p. 2657-2660, (1999).
Klapars et al., "A general and efficient copper catalyst for the amidation of aryl halides and the N-arylation of nitrogen heterocycles," J. Am. Chem. Soc., vol. 123, p. 7727-7729, (2001).
Klapars et al., "A general and efficient copper catalyst for the amidation of aryl halides," J. Am. Chem. Soc., vol. 124, p. 7421-7428, (2002).
Kondratov et al., "Nucelophilic substitution in the aromatic series. Lv. Reaction of o-nitrochlorobenzene with ammonia in the presence of copper compounds," Zhurnal Organidreskoi Khimii, vol. 15, No. 11, p. 2387-2390, (1979).
Koppel, et al., "Optimal treatment of Alzheimer's disease psychosis: challenges and solutions," Neuropsychiatric Disease and Treatment, vol. 10, p. 2253-2262, (2014).
Kumar et al., "Lumateperone: A New Treatment Approach for Neuropsychiatric Disorders," Drugs of Today, vol. 54, No. 12, p. 713-719, (2018).
Kwong et al., "Mild and efficient copper-catalyzed amination of aryl bromides with primary alkylamines," Organic Letters, vol. 5, No. 6, p. 793-796, (2003).
Lebert et al., "Trazodone in Fronto-Temporal Dementia", Research and Practice in Alzheimer's Disease, vol. 11, p. 356-360, (2006).
Lee et al. "Novel, Highly Potent, Selective 5-HT2A/D2 Receptor Antagonists as Potential Atypical Antipsychotics," Bioorg. Med. Chem. Lett. vol. 13, p. 767-770, (2003).
Li et al., "Discovery of a Tetracyclic Quinoxaline Derivative as a Potent and Orally Active Multifunctional Drug Candidate for the Treatment of Neuropsychiatric and Neurological Disorders", vol. 57, p. 2670-2682 (2014).
Lin, et al., "Dosage and duration of antipsychotic treatment in demented outpatients with agitation or psychosis," Journal of the Formosan Medical Association, vol. 114, p. 147-153, (2015).
Lipschitz et al., "Childhood Posttraumatic Stress Disorder: A Review of Neurobiologic Sequelae", Psychiatric Annals Journal, vol. 28, Issue 8, p. 452-457, (1998).
Lopez, et al., "Psychiatric Symptoms Vary With the Severity of Dementia in Probable Alzheimer's Disease," J. Neuropsychiatry Clin. Neurosci., vol. 15, No. 3, p. 346-353, (2003).
Louie et al., "Palladium-Catalyzed Synthesis of Arylamines from Aryl Halides, Mechanistic Studies lead to Coupling in the Absence of Tin Reagents", Tetrahedron Letters, vol. 36, No. 21, p. 3609-3612, (1995).
Lounkine et al, "Formal Concept Analysis for the Identification of Molecular Fragment Combinations Specific for Active and Highly Potent Compounds," J. Med. Chem., vol. 51, No. 17, p. 5342-5348, (2008).
Madhusoodanan, et al., "Pharmacological management of behavioral symptoms associated with dementia," World J. Psychiatr., vol. 4, No. 4, p. 72-79, (2014).
March et al., Advanced Organic Chemistry; Reactions, Mechanisms and Structures, Fourth Edition, pp. 910-911 (1992).
Marcoux et al., "A general copper-catalyzed synthesis of diaryl ethers," J. Am. Chem. Soc., vol. 119, p. 10539-10540, (1997).
Meeter, et al., "Effect of 5HT on Memory and the Hippocampus: Model and Data," Neuropsychopharmacology, 31:712-720 (2006).
Minzenberg, et al., "Modafinil: A Review of Neurochemical Actions and Effects on Cognition," Neuropsychopharmacology, 33:1477-1502 (2008).
Mohamed et al., "Pharmacotherapy of PTSD in the U.S. Department of Veterans Affairs: diagnostic- and symptom-guided drug selection", J. CLin. Psychiatry, vol. 69, pp. 959-965, (2008).
Morgan et al., "Acoustic Startle in Individuals With Posttraumatic Stress Disorder", Psychiatric Annals Journal, vol. 28, Issue 8, p. 430-434, (1998).
Mulrooney et al., "Recent developments in copper-catalyzed n-arylation with aryl halides," Essay—University of Pennsylvania.
Murakami et al., Chem. Pharm. Bull, vol. 43(8), p. 1281-1286, (1995).
Nagai et al. "Synthesis of 2,3,4,4a,5,9b-hexahydro-1H-pyrido[4,3-b] indole derivatives and their central nervous system activities." Journal of Medicinal Chemistry, vol. 22, No. 6, p. 677-683. (1979).
Newman et al., "Solid-state analysis of the active pharmaceutical ingredient in drug products", Drug Discovery Today, vol. 8, No. 9, p. 898-903 (2003).
Nihon rounen igaku zasshi, vol. 48, No. 3, p. 195-204, (2011 nen). English translation only, 2 pages.

(56) References Cited

OTHER PUBLICATIONS

O'Gorman, et al., "Lumateperone (ITI-007): A Novel Investigational Agent with Broad Therapeutic Potential Across Multiple Neuropsychiatric Disorders," Poster P.1.g.038, European College of Neuropsychopharmacology (ECNP) Congress (2017).

O'Hara, et al., "Serotonin Transporter Polymorphism, Memory, and Hippocampal Volume in the Elderly: Association and Interaction with Cortisol," Mol. Psychiatry, 12(6):544-555 (2007).

Olivier, et al., "Serotonin transporter deficiency in rats contribute to impaired object memory," Genes, Brain and Behavior, 8:829-834 (2009).

Pond et al. "Stereospecific reduction of haloperidol in human tissues". Biochemical Pharmacology, vol. 44, No. 5, p. 867-871 (1992).

Press Release, "Intra-Cellular Therapies Reports Positive Final Results of a Phase II Clinical Trial With ITI-007 in Patients with Sleep Maintenance Insomnia.", Intra-Cellular Therapies, Press Release Date: Mar. 10, 2009, 3 pages, available at: https://ir.intracellulartherapies.com/static-files/375e1667-6457-4cd9-95dc-616ca3b5d02b.

Press Release, "Intra-Cellular Therapies Announces Top-Line Results from the Second Phase 3 Trial of ITI-007 in Patients with Schizophrenia (Study '302)", Intra-Cellular Therapies, Press Release Date: Sep. 28, 2016, 8 pages, available at: https://globenewswire.com/news-release/2016/09/28/875435/0/en/Intra-Cellular-Therapies-Announces-Top-Line-Results-from-the-Second-Phase-3-Trial-of-ITI-007-in-Patients-with-Schizophrenia-Study-302.html.

Press Release, "Intra-Cellular Therapies Announces Additional Results From Phase I/II Clinical Trial for ITI-007 in Healthy Geriatric Subjects and Patients With Dementia.", Intra-Cellular Therapies, Press Release Date: Nov. 21, 2014.

Protective Groups in Organic Synthesis, Third Edition, John Wiley & Sons, Inc., p. 494-505, (1999).

Puig, et al., "Serotonin and Prefrontal Cortex Function: Neurons, Networks, and Circuits," Mol. Neurobiol., 44(3):449-464 (2011).

Rackova et al. "Free Radical Scavenging and Antioxidant Activities of Substituted Hexahydropyridoindoles. Quantitative Structure-Activity Relationships." Journal of Medicinal Chemistry, vol. 49, No. 8, p. 2543-2548. (2006).

Reynolds et al. "Longitudinal change in memory performance associated with HTR2A polymorphism," Neurobiology of Aging, 2006, vol. 27, pp. 150-154 (2006).

Sadighi et al., "A highly active palladium catalyst system for the arylation of anilines," Tetrahedron Letters, vol. 39, p. 5327-5330, (1998).

Satlin, et al., "ITI-007 (Lumateperone) for the Treatment of Agitation in Patients with Dementia, including Alzheimer's Disease," Alzheimer's & Dementia 14(7) (Suppl.): p. 678-79 (2018) (Alzheimer's Assoc. International Conference 2018, summary of Poster P2-032).

Satlin, et al., "ITI-007 (Lumateperone) for the Treatment of Agitation in Patients with Dementia, including Alzheimer's Disease," Poster P2-032, Alzheimer's Assoc. International Conference 2018 (2018).

Savjani et al., "Drug Solubility: Importance and Enhancement Techniques", International Scholarly Research Network Pharmaceutics, vol. 2012, p. 1-10, (2012).

Seltzer "Donepezil: an update" Expert Opinion on Pharmacotherapy, 2007, 8:7 1011-1023 (2007).

Sigel et al., "Tenary Complexes in Solution", Inorganic Chemistry, vol. 13, No. 2, p. 462-465 (1974).

Silver et al., "Multifunctional Pharmacotherapy: What Can We Learn from Study of Selective Serotonin Reuptake Inhibitor Augmentation of Antipsychotics in Negative-Symptom Schizophrenia?," Neurotherapeutics, vol. 6, p. 86-93 (2009).

Singhal et al., "Drug polymorphism and dosage form design: a practical perspective", Advanced Drug Delivery Reviews, vol. 56, p. 335-347 (2004).

Skoog, "Principles of Instrumental Analysis, 4th Edition", p. 577 (1992).

Smith, et al., "Oxford Dictionary of Biochemistry and Molecular Biology", Oxford University Press, p. 145, (1997).

Snyder et al., "Functional profile of a novel modulator of serotonin, dopamine, and glutamate neurotransmission", Psychopharmacology, Published online Aug. 2014, DOI 10.1007/s00213-014-3704-1.

Snyder et al., "Functional profile of a novel modulator of serotonin, dopamine, and glutamate neurotransmission", Psychopharmacology, vol. 232, p. 605-621 (2015).

Southwick et al., "Neuroendocrine Alterations in Posttraumatic Stress Disorder", Psychiatric Annals Journal, vol. 28, Issue 8, p. 436-442, (1998).

Sugahara et al., "A Facile Copper-Catalyzed Ullman Condensation: N-Arylation of Heterocyclic Compounds Containing an -NHCO-Moiety", Chem. Pharm. Bull., vol. 45, No. 4, p. 719-721, (1997).

Taragano, et al., "A Double-Blind, Randomized, Fixed-Dose Trial of Fluoxetine vs. Amitriptyline in the Treatment of Major Depression Complicating Alzheimer's Disease," Psychosomatics, vol. 38, p. 246-252, (1997).

Tariot, et al., "Memantine Treatment in Patients with Moderate to Severe Alzheimer Disease Already Receiving Donepezil," JAMA, vol. 291, No. 3, p. 317-324, (2004).

Vanover, et al., "Lumateperone (ITI-007): A Novel Investigational Agent with Broad Therapeutic Potential Across Multiple Neuropsychiatric Disorders," *European Neuropsychopharmacology*, 27:S660-61 (2017) (Summary of ECNP Poster P.1.g.038).

Vloeberghs et al., "Altered Circadian Locomotor Activity in APP23 Mice: A Model for BPSD Disturbances," *Eur J Neuroscience*, vol. 20, pp. 2757-2766, (2004).

Wagaw et al., "A palladium-catalyzed method for the preparation of indoles via the Fischer indole synthesis," Journal of the American Chemical Society, vol. 121, No. 44, p. 10251-10263, (1999).

Weschules et al., "Acetylcholinesterase Inhibitor and N-Methyl-D-Aspartic Acid Receptor Antagonist Use among Hospice Enrollees with a Primary Diagnosis of Dementia", Journal of Palliative Medicine, vol. 11, No. 5, p. 738-745, (2008).

Wolfe et al., "An improved catalyst system for aromatic carbon-nitrogen bond formation: The possible involvement of bis(phosphine) palladium complexes as key intermediates," JACS, vol. 118, p. 7215-7216, (1996).

Wolfe et al., "Intramolecular palladium-catalyzed aryl amination and aryl amidation," Tetrahedron, vol. 52, No. 21, p. 7525-7546, (1996).

Wolter et al., "Synthesis of N-aryl hydrazides by copper-catalyzed coupling of hydrazides with aryl iodides," Organic Letters, vol. 3, No. 23, p. 3803-3805, (2001).

Xu, et al., "Neurotransmitter receptors and cognitive dysfunction in Alzheimer's disease and Parkinson's disease," Progress in neurobiology, 97(1):1-13 (2012).

Yamada et al., "A mild copper-mediated intramolecular amination of aryl halides," Synlett, No. 2, p. 231-234, (2002).

Yang et al., "The development of efficient protocols for the palladium-catalyzed cyclization reactions of secondary amides and carbamates," Organic Letters, vol. 1, No. 1, p. 35-37, (1999).

Yiannopoulou, et al., "Current and future treatments for Alzheimer's disease," Therapeutic Advances in Neurological Disorders, 6(1):19-33 (2013).

Zhang et al., "Highly efficient copper-catalyzed N-arylation of alkylamines with aryl iodides using phosphoramidite as ligand", Catalysis Communications, vol. 6, p. 784-787, (2005).

Zhang et al., "The Role of Serotonin 5-HT2A Receptors in Memory and Cognition," Front Pharmacol., vol. 6, No. 225, p. 1-17, (2015); DOI: 10.3389/fphar.2015.00225.

"Clinical Trial Evaluating ITI-007 (Lumateperone) as a Monotherapy for the Treatment of Bipolar," ClinicalTrials.gov (Identifier: NCT02600494), 5 pages, (2015).

"Clinical Trial Evaluating ITI-007 as an Adjunctive Therapy to Lithium or Valproate for the Treatment of Bipolar Depression," ClinicalTrials.gov, 6 pages, Nov. 9, 2015.

"Highlights of Prescribing Information Caplyta (lumateperone) capsules, for oral use," Label—Prescribing Information, 16 pages, (2019); https://www.accessdata.fda.gov/drugsatfda_docs/label/2019/209500s000lbl.pdf.

(56) References Cited

OTHER PUBLICATIONS

"Study of a Novel Antipsychotic ITI-007 in Schizophrenia," Clinical Trials.gov, 6 pages, Dec. 26, 2011.
Cascade, E. et al., "Antidepressants in Bipolar Disorder," Psychiatry (Edgmont), vol. 4, No. 3, pp. 56-58, 1 page, (2007).
Celada, P. et al., "The Therapeutic Role of 5-HT1A and 5-HT2A Receptors in Depression," Rev. Psychiatr. Neurosci., vol. 29, No. 4, pp. 252-265, 14 pages, (2004).
Citrome, L. et al., "Toward Convergence in the Medication Treatment of Bipolar Disorder and Schizophrenia," Harv. Rev. Psychiatry, vol. 13, No. 1, p. 28-42 (2005).
Cole, P. et al., "ITI-007. 5HT2A Receptor Antagonist, Dopamine D2 Receptor Modulator, Treatment of Schizophrenia, Treatment of Insomnia," Drugs of the Future, vol. 40, No. 1, pp. 643-650, (2015).
Corponi, F. et al., "Novel Antipsychotics Specificity Profile: A Clinically Oriented Review of Lurasidone, Brexpiprazole, Cariprazine and Lumateperone," European Neuropsychopharmacology, vol. 29, pp. 971-998, (2019).
Correa-Illanes, G., "Neuropathic Pain, Clasification and Management for General Practicioners," Rev. Med. Clin. Condes, vol. 25, No. 2, pp. 189-199, (2014), English summary on p. 1.
Davis, R. et al., "ITI-007 in the treatment of schizophrenia: from novel pharmacology to clinical outcomes," Expert Review of Neurotherapeutics, vol. 16, No. 6, pp. 601-614 (2016).
Dutheil, S., et al. "Lumateperone Normalizes Pathological Levels of Acute Inflammation through Important Pathways Known to Be Involved in Mood Regulation," The Journal of Neuroscience, vol. 43, No. 5, pp. 863-877, (2023).
Ghaemi, N., "Expert Commentary—Antidepressants in Bipolar Disorder," Psychiatry (Edgmont), vol. 4, No. 3, p. 56-58 (2007).
Harvey, P. et al., "Lumateperone Improves Negative Symptoms Related to Emotional Experience (Avolition) in Patient with Schizophrenia," Abstract presented at the American Society of Clinical Psychopharmacology (ASCP) Annual Meeting: May 29-Jun. 1, 2018: Miami, FL.
Liebermann, J. et al., "ITI-007 for the Treatment of Schizophrenia: A 4-Week Randomized, Double-Blind, Controlled Trial," Biological Psychiatry, vol. 79, pp. 952-961, (2016).
Marek, G. et al., "Synergistic Action of 5-HT2A Antagonists and Selective Serotonin Reuptake Inhibitors in Neuropsychiatric Disorder," Neuropsychopharmacology, vol. 28, pp. 402-412, (2003).
Mazza, M. et al., "Evidence on the New Drug Lumateperone (ITI-007) for Psychiatric and Neurological Disorders," CNS & Neurological Disorders—Drug Targets, vol. 19, pp. 243-247, (2020).
Montgomery, S. et al., "Pharmacotherapy of Depression and Mixed States in Bipolar Disorder," J. Affect. Disord., vol. 59, pp. S39-S56, 18 pages, (2000).
Press Release, "Intra-Cellular Therapies Announces Positive Top-Line Results from a Phase 3 Trial of Lumateperone in Patient with Bipolar Depression," Intra-Cellular Therapies, Press Release Date: Jul. 8, 2019.
Press Release, "Intra-Cellular Therapies Announces Successful Outcome of a Phase II Clinical Trial With Iti-007 in Patients With Sleep Maintenance Insomnia," Intra-Cellular Therapies Inc., Press Release Date: Jan. 13, 2009.
Press Release, "Intra-Cellular Therapies Presents Data on Symptom Improvement by Lumateperone on Negative Symptoms, Depression, and Social Function in Patients with Schizophrenia at the American Society of Clinical Psychopharmacology (ASCP) Annual Meeting," Intra-Cellular Therapies, Press Release Date: May 31, 2018, (https://ir.intracellulartherapies.com/newsreleases/.
Satlin, A. et al., "W203: Additional Results from a 12-Month Open-Label Safety Study of Lumateperone (ITI-007) in Patients with Stable Symptoms of Schizophrenia," ACNP 58th Annual Meeting: Poster Session III, vol. 44, Suppl. 1. pp. 493-494, (2019).
Snyder, G. et al., "Chapter 11: A review of the pharmacology and clinical profile of lumateperone for the treatment of schiophrenia," Advances in Pharmacology, vol. 90, pp. 253-276, 31 pages, (2021).
Vanover, K. et al., "50. ITI-007, an Investigational New Antipsychotic Drug with a Novel Pharmacological Profile, is Safe and Well-Tolerated with Early Clinical Signs for Efficacy in Patients with Stabilized Schizophrenia," Abstract presented at the ANCP 49th Annual Conference in Poster Session III; Dec. 8, 2010; pp. S321-S322; Neuropsychopharmacology, vol. 35, (2010).
Vanover, K. et al., "Dopamine D2 receptor occupancy of lumateperone (ITI-007): a Positron Emission Tomography Study in patients with schizophrenia," Neuropsychopharmacology, vol. 44, pp. 598-605, (2018).
Vanover, K. et al., "ITI-007: A Novel Therapy for the Treatment of Schizophrenia and Related Psychoses," International Clinical Psychopharamcology, vol. 26, e56, 1 page, (2011).
Vanover, K. et al., "Pharmacokinetic Profile of ITI-007, A Novel Approach for the Treatment of Schizophrenia and Other Psychiatric and Neurological Disorders" Neuropsychopharmacology, vol. 38 (2012), p. S418 (ACNP 51st Poster Session III: Abstract No. W176).
Vanover, K. et al., "Safety, Pharmacokinetics and Early Signals for Efficacy with ITI-007, A Novel Investigational New Drug for the Treatment of Schizophrenia and Related Disorders," Schizophrenia Bulletin, vol. 37, Suppl. 1, p. 325, (2011), Abstract only.
Vanover, K. et al., "T184. Long-Term Safety for Lumateperone (ITI-007) in the Treatment of Schizophrenia," ANCP 57th Annual Meeting: Poster Session II, 4 pages, (2018).
Vanover, K. et al., "W201. Efficacy and Safety of Lumateperone 42 mg in the Treatment of Schizophrenia: A Pooled Analysis of Randomized Clinical Trials," ACNP 58th Annual Meeting: Poster Session III, vol. 44, Suppl. 1, pp. 492-494, Dec. 5, 2019.
Vanover, K. et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting, May 29-Jun. 1, 2018; Miami, FL.
Vanover, K. et al., Abstracts of the 13th International Congress on Schizophrenia (ICOSR) (Apr. 2-6, 2011), Schizophrenia Bull., vol. 37, Suppl. 1., p. 325, (2011).
Vyas, P. et al., "An Evaluation of Lumateperone Tosylate for the Treatment of Schizophrenia," Expert Opinion on Pharmacotherapy, vol. 21, No. 2, pp. 139-145, (2020); https://doi.org/10.1080/14656566.2019.1695778.
Wennogle, L. et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.
Yatham, L., "Atypical Antipsychotics for Bipolar Disorder," Psychiatr. Clin. N. Am., vol. 28, No. 2, p. 325-347 (2005).

* cited by examiner

COMPOUNDS AND METHODS

CROSS REFERENCE TO RELATED APPLICATIONS

This application is a continuation of U.S. application Ser. No. 17/405,736, filed on Aug. 18, 2021, which is a continuation of U.S. application Ser. No. 16/585,251, filed on Sep. 27, 2019, which is a continuation of U.S. application Ser. No. 14/394,470, filed on Oct. 14, 2014, which is a national stage application filed under 35 U.S.C. § 371 of International Application No. PCT/US2013/036515, filed on Apr. 14, 2013, which is an International Application which claims priority from U.S. Provisional Application Nos. 61/624,293, 61/624,292 and 61/624,291, all filed on Apr. 14, 2012; and U.S. Provisional Application Nos. 61/671,723 and 61/671,713, both filed on Jul. 14, 2012, the contents of each of which are incorporated by reference in their entirety.

TECHNICAL FIELD

The present invention relates to use of particular substituted heterocycle fused gamma-carbolines as described herein, in free, pharmaceutically acceptable salt or prodrug form, and pharmaceutical composition comprising the same, optionally in combination with one or more agents, for the prophylaxis or treatment of one or more disorders associated with dementia, particularly behavioral or mood disturbances (e.g., agitation/aggression), psychosis, depression and/or sleep disturbances among other disorders in patients suffering from dementia.

BACKGROUND OF THE INVENTION

Dementia is a disorder characterized by the loss of cognitive abilities affecting memory, reasoning, judgment and behavior. At an early stage of dementia, people may experience mild cognitive impairment (MCI, also known as incipient dementia, or isolated memory impairment) which is cognitive impairment beyond that expected based on the age and education of the individual, but which is not significant enough to interfere with their daily activities. Studies suggest that these individuals tend to progress to probable Alzheimer's disease at a rate of approximately 10% to 15% per year. Alzheimer's disease is the most common type of dementia and is an irreversible, progressive neurodegenerative disease that disrupts memory, perception, reasoning, judgment, information processing, emotional behavior, personality as well as social and occupational functions. Of date, 5.4 million of Americans are believed to be living with Alzheimer's and nearly 36 million people worldwide are believed to be living with this disease or other dementias.

Currently, there is no cure or standard of treatment for dementia. Available treatments are palliative and symptomatic in nature aiming to manage and slow the progression of the cognitive manifestation of the disease. Drugs approved in the United States for the treatment of Alzheimer's disease, which is also used to treat dementia in general include acetylcholinesterase inhibitors (e.g., Tacrine, rivastigmine (Exelon), donepezil (Aricept), and galantamine (Razadyne, formerly called Reminyl)) and NMDA receptor antagonist (e.g., memantine (Namenda)). While these drugs improve mental function (such as memory, attention, social interaction, reasoning ability, language ability, and ability to perform activities of daily living), they often cause side effects including stomach upset, diarrhea, nausea, vomiting, muscle cramps, fatigue, difficulty falling or staying asleep or excess sleepiness, depression, bradycardia and other side effects. In addition, these drugs do not treat affective symptoms and/or other behavior disruptions such as mood swing, agitation, aggressive/assaultive behavior and paranoia which are common in dementias. In fact, some studies have shown that memantine, a drug approved for Alzheimer's disease and often used for dementias in general, may have some adverse effects on neuropsychiatric functioning, particularly agitation/aggression, delusions or hallucinations. These untreated and sometimes aggravated behavioral disruptions often prevent the patients from integrating back into society, causing further distress to the caregivers and eventually leading to the patients' institutionalization. To control aggression and psychosis in dementia, particularly in Alzheimer's disease, antipsychotic drugs are used. However, antipsychotic drugs such as haloperidol, risperidone and quetiapine are associated with serious side effects including extrapyramidal side effects (akinesia or akathisia), bone marrow suppression, seizure, orthostatic hypotension, insomnia, sedation, somnolence and weight gain. Many atypical antipsychotic agents also have a higher risk of heart failure. Therefore, the use of these antipsychotic agents in combination with anticholinesterase inhibitor or NMDA receptor antagonist is undesirable.

In addition to behavior and mood disturbances, many dementia patients, particularly those at a more serious stage of the disease also commonly experience sleep disturbances wherein the patients either have difficulty falling asleep, maintaining sleep or experience changes in their sleep-wake cycle/pattern. These patients may also feel restless or agitated in the late afternoon or early evening (often called "sundowning"). In fact, studies have shown evidence that a loss in the suprachiasmatic nucleus (SCN) neuronal population coincides with Alzheimer's patients' stage of dementia. This loss of SCN neuronal population appears to be causative in the observed disturbances in melantonin rhythm which may underlie accompanying sleep disturbances. While agents such as temazepam (Restoril), zolpidem (Ambien), or zaleplon (Sonata), or sedating antidepressants, such as trazodone (Desyrel, Molipaxin), may be useful in managing insomnia, failure of these drugs to improve sleep quality in addition to the associated risk of falling due to drowsiness and psychomotor impairment caused by these agents render them undesirable for dementia, particularly Alzheimer's patients.

There remains an urgent need for an effective therapeutic regime for the prophylaxis or treatment of dementia and disorders associated thereof, particularly to alleviate behavioral/mood disturbances (e.g., agitation, aggressive/assaultive behavior) and sleep disturbances in patients suffering from dementia.

Substituted heterocycle fused gamma-carbolines are known to be agonists or antagonists of 5-HT2 receptors, particularly 5-HT2A and 5-HT2C receptors, in treating central nervous system disorders. These compounds have been disclosed in U.S. Pat. Nos. 6,548,493; 7,238,690; 6,552,017; 6,713,471; RE39,680, and RE39,679, as novel compounds useful for the treatment of disorders associated with 5-HT2A receptor modulation such as obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility. PCT/US08/03340 and U.S. Pat. No. 7,081,455 also disclose methods of making substituted heterocycle fused gamma-carbolines and uses of these gamma-carbolines as serotonin agonists and antagonists useful for the control and prevention of central nervous system disorders such as addictive behavior and sleep disorders. WO 2009/145900 discloses use of specific compounds of substituted heterocycle fused gamma-carbolines for the treatment of a combination of psychosis and depressive disorders as well as sleep, depressive and/or mood disorders in patients with psychosis or Parkinson's disease. These references, however, do not teach use for the treatment or prophylaxis of disorders associated with dementia, particularly behavioral or mood disturbances such as agitation, irritation, aggressive/assaultive behavior, anger, physical or emotional outbursts and psychosis and sleep disorders associated with dementia.

SUMMARY OF THE INVENTION

It has been discovered that the Compounds of the Invention (i.e., the Compounds of Formula I as described hereinbelow) fully saturate 5-$HT_{2A}$ receptors at a low dose. Altered serotonergic function has consistently been implicated in the pathophysiology of aggression. In animal models, 5-$HT_{2A}$ antagonists attenuate aggressive & impulsive behaviors. Human platelet 5-$HT_{2A}$ levels are associated with aggression in personality disordered patients, but not in healthy control subjects. Postmortem studies also show that 5-$HT_{2A}$ receptor expressions in prefrontal cortical regions are correlated positively with lifetime aggression in subjects who committed suicide. Orbitofrontal 5-$HT_{2A}$ receptor availability is greater in patients with current physical aggression compared with patients without current physical aggression and healthy control subjects. Specific genetic polymorphisms of 5-$HT_{2A}$ receptors are associated with aggression and impulsivity. These Compounds also exhibit efficacy in reducing behavioral disturbances such as agitation and irritability as well as sleep disturbances and symptoms of depression and psychosis. Due to their low off target receptor interactions, the Compounds of the Invention have reduced sedation, cognitive impairment, motor impairment and lower risk of falls. Therefore, Compound of Formula I as described below are effective in treating 5-HT2A related disorders without having the extrapyramidal side effects, psychomotor sedation, cognitive impairment or cardiovascular safety issues such as QTc prolongation. This discovery gives the Compounds of the current Invention particular utility in the treatment or prophylaxis of one or more disorders associated with dementia, particularly behavioral or mood disturbances such as agitation, irritation, aggressive/assaultive behavior, anger, physical or emotional outbursts and sleep disturbances, which conditions are often left untreated by current marketed drugs, as well as psychosis and depressive disorders in dementia patients.

Therefore, in the first aspect, the invention provides a method (Method I) for the prophylaxis or treatment of one or more disorders associated with dementia, e.g., disorders associated with mild cognition impairment and dementing illnesses including senile dementia, Alzheimer's disease, Pick's disease, frontotemporal dementia, parasupranculear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease, comprising administering to a patient in need thereof, a therapeutically effective amount of a compound of Formula I:

Formula I

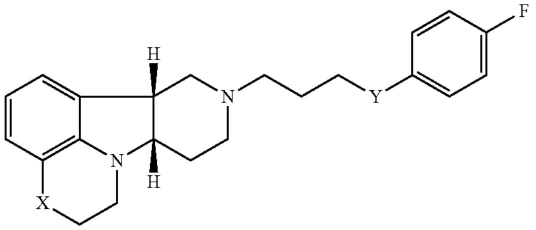

wherein:

X is —N(H)—, —N($CH_3$)— or —O—;

Y is —C(=O), —C(H)(OH) or —C(H)($OR_1$);

$R_1$ is —C(O)—$C_{1-21}$alkyl (e.g., —C(O)—$C_{1-5}$alkyl, —C(O)—$C_{6-15}$alkyl or —C(O)—$C_{16-21}$alkyl), preferably said alkyl is a straight chain, optionally saturated or unsaturated and optionally substituted with one or more hydroxy or $C_{1-22}$alkoxy (e.g., ethoxy) groups, for example $R_1$ is —C(O)—$C_6$alkyl, —C(O)—$C_7$alkyl, C(O)—$C_9$alkyl, —C(O)—$C_{11}$alkyl, —C(O)—$C_{13}$alkyl or —C(O)—$C_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand), in free, pharmaceutically acceptable salt or prodrug form.

In a further embodiment, the invention provides the following formulae:

1.1. Method I, wherein X in the compound of Formula I is —N(H)—, —N($CH_3$)— or —O—;

1.2 Method I or 1.1, wherein X in the compound of Formula I is —N(H);

1.3. Method I or 1.1, wherein X in the compound of Formula I is —N($CH_3$)—;

1.4. Method I or 1.1, wherein X in the compound of Formula I is —O—;

1.5. Method I or any of formulae 1.1-1.4, wherein Y in the compound of Formula I is —C(=O), —C(H)(OH) or —C(H)($OR_1$);

1.6 Method I or any of formulae 1.1-1.4, wherein Y in the compound of Formula I is —C(=O);

1.7. Method I or any of formulae 1.1-1.4, wherein Y in the compound of Formula I is —C(H)(OH);

1.8. Method I or any of formulae 1.1-1.4, wherein Y in the compound of Formula I is —C(H)($OR_1$);

1.9. Method I or 1.8, wherein $R_1$ is —C(O)—$C_{1-21}$alkyl (e.g., —C(O)—$C_{1-5}$alkyl, —C(O)—$C_{6-15}$alkyl or —C(O)—$C_{16-21}$alkyl), preferably said alkyl is a straight chain, optionally saturated or unsaturated and optionally substituted with one or more hydroxy or $C_{1-22}$alkoxy (e.g., ethoxy) groups, for example $R_1$ is —C(O)—$C_6$alkyl, —C(O)—$C_7$alkyl, —C(O)—$C_9$alkyl, —C(O)—$C_{11}$alkyl, —C(O)—$C_{13}$alkyl or —C(O)—$C_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand);

1.10. Method I or 1.8, wherein $R_1$ is —C(O)—$C_{6-15}$alkyl, e.g., —C(O)—$C_9$alkyl;

1.11. Method I or 1.8, wherein $R_1$ is —C(O)—$C_{1-5}$alkyl, e.g., —C(O)—$C_3$alkyl;

1.12. Method I or any of formulae 1.1-1.5 or 1.7, wherein the Compound is:

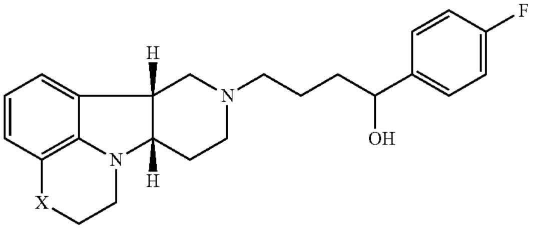

1.13. Method I or any of formulae 1.1-1.5 or 1.7, wherein the Compound is:

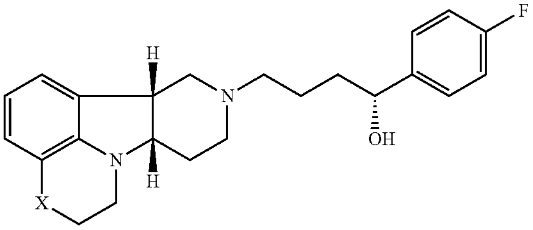

1.14. Method I or any of formulae 1.1-1.5 or 1.7, wherein the Compound is:

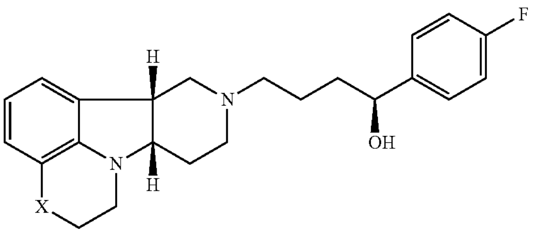

1.15. Method I or any of formulae 1.1, 1.3, 1.5 or 1.7, wherein the Compound is:

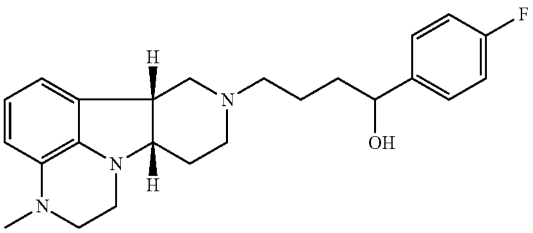 [SMILES: CN1CCN2c3c(cccc31)[C@@H]1CN(CCCC(O)c3ccc(F)cc3)CC[C@@H]12]

1.16. Method I or any of formulae 1.1, 1.3, 1.5 or 1.6, wherein the Compound is:

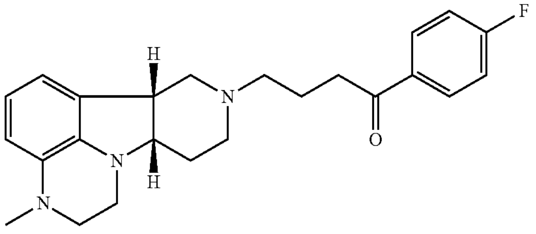 [SMILES: CN1CCN2c3c(cccc31)[C@@H]1CN(CCCC(=O)c3ccc(F)cc3)CC[C@@H]12]

1.17. Method I or any of formulae 1.1, 1.3, 1.5, 1.8 or 1.9, wherein the Compound is:

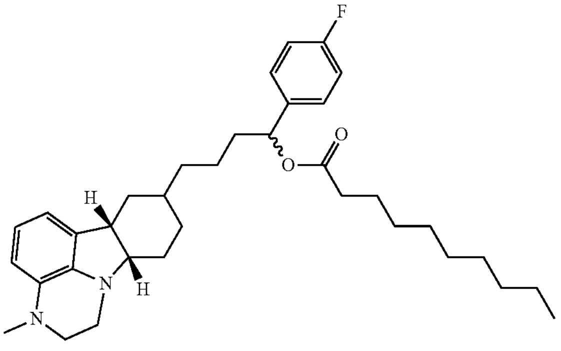 [SMILES: CCCCCCCCCC(=O)OC(CCCC1CC[C@H]2[C@@H](C1)c1cccc3c1N2CCN3C)c1ccc(F)cc1]

1.18. Method I or any of formulae 1.1, 1.3, 1.5, 1.8 or 1.9, wherein the Compound is:

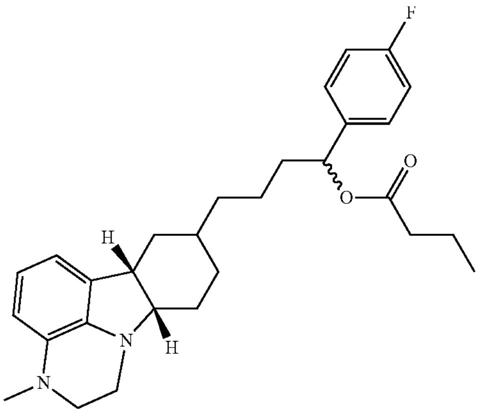, in free, pharmaceutically acceptable salt or prodrug form.

In a further embodiment of the first aspect, the invention provides Method I as follows:

2.1. Method I or any of 1.1-1.18, wherein the disorders associated with dementia are disorders associated with Huntington's disease, Parkinson's disease, Multiple sclerosis, Amyotrophic lateral sclerosis, Down syndrome, Elderly depression, Wernicke-Korsakoff's syndrome, corticobasal degenerations, and prion disease;

2.2. Method I or any of 1.1-1.18, wherein the disorders associated with dementia are disorders associated with mild cognition impairment and dementing illnesses including senile dementia, Alzheimer's disease, Pick's disease, frontotemporal dementia, parasupranculear palsy, dementia with Lewy bodies and vascular dementia;

2.3. Method I or any of 1.1-1.18 or 2.1, wherein the disorders associated with dementia are disorders associated with senile dementia, Alzheimer's disease, Pick's disease, frontotemporal dementia, parasupranculear palsy, dementia with Lewy bodies and vascular dementia;

2.4. Method I or any of 1.1-1.18 or 2.1, wherein the disorders associated with dementia are disorders associated with Alzheimer's disease;

2.5. Method I or any of 1.1-1.18 or 2.1, wherein the disorders associated with dementia are disorders associated with mild cognition impairment;

2.6. Method I or any of 1.1-1.18 or 2.1-2.5, wherein the disorder associated dementia to be treated is selected from the group consisting of (1) behavioral or mood disorders such as agitation/irritation, aggressive/assaultive behavior, anger, physical or emotional outbursts; (2) psychosis; (3) depression; and (4) sleep disorders in patients suffering from dementia, particularly Alzheimer's disease;

2.7. Method I or any of 1.1-1.18 or 2.1-2.6, wherein the disorder to be treated is psychosis in a patient with dementia, particularly Alzheimer's disease;

2.8. Method I or any of 1.1-1.18 or 2.1-2.7, wherein the disorder to be treated is depression in a patient with dementia, particularly Alzheimer's disease;

2.9. Method I or any of 1.1-1.18 or 2.1-2.8, wherein the dosage of the Compound of Formula I, or any of 1.1-1.18 is 10-100 mg;

2.10. Method I or any of 1.1-1.18 or 2.1-2.9, wherein the disorder to be treated is behavioral or mood disorders such as agitation/irritation, aggressive/assaultive behavior, anger, physical or emotional outbursts in a patient with dementia, particularly Alzheimer's disease;

2.11. Method I or any of 1.1-1.18 or 2.1-2.10, wherein the disorder to be treated is sleep disorders in a patient with dementia, particularly Alzheimer's disease;

2.12. Method I or any of 1.1-1.18 or 2.1-2.11, wherein the disorder to be treated is sleep maintenance insomnia, frequent awakenings, and waking up feeling unrefreshed in a patient with dementia, particularly Alzheimer's disease;

2.13. Method I or any of 1.1-1.18 or 2.1-2.12, wherein the disorder to be treated is sleep maintenance insomnia in a patient with dementia, particularly Alzheimer's disease;

2.14. Method I or any of 1.1-1.18 or 2.1-2.12, wherein the disorder to be treated is advanced sleep-phase syndrome in a patient with dementia, particularly Alzheimer's disease;

2.15. Method I or any of 1.1-1.18 or 2.1-2.12, wherein the disorder to be treated is delayed sleep-phase syndrome in a patient with dementia, particularly Alzheimer's disease;

2.16. Method I or any of 1.1-1.18, 2.1-2.6 or 2.10-2.15, wherein the dosage of the Compound of Formula I, or any of 1.1-1.18 is 1-10 mg;

2.17. Method I or any of 1.1-1.18 or 2.1-2.16, further comprises administering one or more therapeutic agents useful for the prophylaxis or treatment of dementia, particularly Alzheimer's disease;

2.18. Method I or any of 1.1-1.18 or 2.17, wherein the therapeutic agent useful for the prophylaxis or treatment of dementia, particularly Alzheimer's disease is a cholinesterase inhibitor (e.g., acetylcholinesterase inhibitor) or an N-Methyl D-Asparate (NMDA) receptor antagonist, in free or pharmaceutically acceptable salt form;

2.19. Method I or any of 1.1-1.18 or 2.17-2.18, wherein the cholinesterase inhibitor (e.g., acetylcholinesterase inhibitor) is selected from the group consisting of Tacrine, rivastigmine (Exelon), donepezil (Aricept), and galantamine (Razadyne, formerly called Reminyl)) in free or pharmaceutically acceptable salt form;

2.20. Method I or any of 1.1-1.18 or 2.17-2.19, wherein the cholinesterase inhibitor (e.g., acetylcholinesterase inhibitor) is donepezil in free or pharmaceutically acceptable salt form;

2.21. Method I or any of 1.1-1.18 or 2.17-2.18, wherein the NMDA receptor antagonist is memantine in free or pharmaceutically acceptable salt form;

2.22. Method I or any of 1.1-1.18 or 2.17-2.18, wherein the therapeutic agent useful for the prophylaxis or treatment of dementia, particularly Alzheimer's disease is a combination of a cholinesterase inhibitor (e.g., acetylcholinesterase inhibitor) and an N-Methyl D-Asparate (NMDA) receptor antagonist, in free or pharmaceutically;

2.23. Method I or any of 1.1-1.18 or 2.22, wherein the one or more therapeutic agent(s) useful for the prophylaxis or treatment of dementia, particularly Alzheimer's disease or symptoms thereof is a combination of donepezil and memantine in free or pharmaceutically acceptable salt form.

2.24. Method I or any of the foregoing methods further comprises administering one or more therapeutic agents selected from antidepressant compounds, compounds that modulate GABA activity (e.g., enhances the activity and facilitates GABA transmission), a GABA-B agonist, a 5-HT modulator (e.g., a 5-$HT_{1A}$ agonist, a 5-$HT_{2A}$ antagonist, a 5-$HT_{2A}$ inverse agonist, etc.), a melatonin agonist, an ion channel modulator (e.g., blocker), a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug, and an antipsychotic agent, e.g., an atypical antipsychotic agent, in free or pharmaceutically acceptable salt form.

In a second aspect, the invention provides a pharmaceutical composition (Pharmaceutical Composition I) comprising the compound of Formula I or any of formulae 1.1-1.18 in combination with one or more therapeutic agents useful for the prophylaxis or treatment of one or more disorders associated with dementia, e.g., disorders associated with mild cognition impairment and dementing illnesses including senile dementia, Alzheimer's disease, Pick's disease, frontotemporal dementia, parasupranculear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease in admixture with a pharmaceutically acceptable diluent or carrier.

In a further embodiment of the second aspect, the invention provides the Pharmaceutical Composition I as hereinbefore described wherein the therapeutic agent(s) useful for the prophylaxis or treatment of one or more disorders associated with dementia, e.g., disorders associated with mild cognition impairment and dementing illnesses including senile dementia, Alzheimer's disease, Pick's disease, frontotemporal dementia, parasupranculear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease, is a cholinesterase inhibitor (e.g., acetylcholinesterase inhibitor) or an N-Methyl D-Asparate (NMDA) receptor antagonist) as described in any of formulae 2.17-2.23.

In another embodiment of the second aspect, the invention provides the Pharmaceutical Composition I as hereinbefore described wherein the therapeutic agent(s) useful for the prophylaxis or treatment of one or more disorders associated with dementia is selected from: antidepressant compounds, compounds that modulate GABA activity (e.g., enhances the activity and facilitates GABA transmission), a GABA-B agonist, a 5-HT modulator (e.g., a 5-$HT_{1A}$ agonist, a 5-$HT_{2A}$ antagonist, a 5-$HT_{2A}$ inverse agonist, etc.), a melatonin agonist, an ion channel modulator (e.g., blocker), a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug, and an antipsychotic agent, e.g., an atypical antipsychotic agent, in free or pharmaceutically acceptable salt form.

In a third aspect, the invention provides a pharmaceutical composition comprising the Compound of Formula I or any of formulae 1.1-1.18 in admixture with a pharmaceutically acceptable diluent or carrier, or the Pharmaceutical Composition I as hereinbefore described, for use (in the manufacture of a medicament) for the prophylaxis or treatment of one or more disorders associated with dementia, e.g., disorders associated with mild cognition impairment and dementing illnesses including senile dementia, Alzheimer's disease, Pick's disease, frontotemporal dementia, parasupranculear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease, as disclosed in Method I or any of formulae 2.1-2.24.

In the fourth aspect, the invention provides use of the Compound of Formula I or any of formulae 1.1-1.18 (in the manufacture of a medicament) for the prophylaxis or treatment of one or more disorders associated with dementia, e.g., one or more disorders associated with mild cognition impairment and dementing illnesses including senile dementia, Alzheimer's disease, Pick's disease, frontotemporal dementia, parasupranculear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease, as disclosed in Method I or any of formulae 2.1-2.24.

In the fifth aspect, the invention provides the Pharmaceutical Composition of the Invention as described herein for use in the manufacture of a medicament for the prophylaxis or treatment of one or more disorders associated with dementia, e.g., disorders associated with mild cognition impairment and dementing illnesses including senile dementia, Alzheimer's disease, Pick's disease, frontotemporal dementia, parasupranculear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease as disclosed in Method I or any of formulae 2.1-2.24.

DETAILED DESCRIPTION

The Compounds of the Invention as hereinbefore described have a selective receptor profile wherein they fully saturate the 5-$HT_{2A}$ receptors at a low dose and also bind to dopamine receptors and serotonin reuptake transporter (SERT) at a higher dose. Therefore the Compounds of the Invention are effective in treating one or more disorders associated with dementia, e.g., one or more disorders associated with mild cognition impairment and dementing illnesses including senile dementia, Alzheimer's disease, Pick's disease, frontotemporal dementia, parasupranculear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease, particularly behavioral/mood disturbances (e.g., agitation, aggressive/assaultive behavior) and sleep disorders, which are inadequately treated by the current marketed drugs for dementia and Alzheimer's disease, as well as treating psychosis and depressive disorders in patients suffering from dementia. The compounds of the Invention (i.e., Formula I as hereinbefore described) may be used in a combination therapy wherein the Compound of Formula I may be administered simultaneously, separately or sequentially with another active agent to treat dementia or dementing illnesses as hereinbefore described, particularly Alzheimer's disease or symptoms thereof.

The Compound of Formula I, in free, pharmaceutically acceptable salt or prodrug form may be administered in a composition, wherein said Compound of Formula I as hereinbefore described in free, pharmaceutically acceptable salt or prodrug form, is in admixture with a pharmaceutically acceptable diluent or carrier. Wherein the Compound of Formula I is administered in a combination therapy, the combination may be administered as a fixed combination (wherein the therapeutic agents are in a single dosage form, e.g., the Pharmaceutical Composition I hereinbefore described) or as a free combination (wherein therapeutic agents are in a separate dosage form).

The second or further therapeutic agents useful for the prophylaxis or treatment of dementia as hereinbefore described, particularly Alzheimer's disease described in Method I or any of formulae 2.17-2.24 of the invention include but not limited to a cholinesterase inhibitor and/or N-Methyl D-Asparate (NMDA) receptor antagonist.

Cholinesterase inhibitors, e.g., acetylcholinesterase inhibitors, are known in the art and/or are described e.g., in U.S. Pat. Nos. 4,895,841; and 4,948,807, the contents of each of which are incorporated by reference in their entirety. Preferred cholinesterase inhibitors to be used with the compound of the present invention include donepezil, rivastignmine, galantamine and tacrine.

NMDA receptor antagonists are also known in the art and are described in U.S. Pat. No. 5,061,703, the contents of which are incorporated by reference in their entirety. Preferred NMDA receptor antagonist to be used with the compound of the present invention is memantine.

Unlike dopamine receptor antagonists, Compounds of Formula I normalize brain dopamine activity, particularly in the prefrontal cortex. The Compounds of Formula I bind to 5-$HT_{2A}$ and dopamine $D_2$ receptors. Compounds of Formula I also exhibit nanomolar binding affinity for SERT compared to known antidepressants. Therefore, the compounds of Formula I are useful for the treatment of (1) behavioral or mood disorders such as agitation/irritation, aggressive/assaultive behavior, anger, physical or emotional outbursts; (2) psychosis; (3) depression; and (4) sleep disorders in patients suffering from dementia, particularly Alzheimer's disease. Therefore, in addition to the therapeutic agents useful for the treatment of dementia, the methods of the invention as hereinbefore described may optionally further comprises one or more therapeutic agents selected from antidepressant compounds, compounds that modulate GABA activity (e.g., enhances the activity and facilitates GABA transmission), a GABA-B agonist, a 5-HT modulator (e.g., a 5-$HT_{1A}$ agonist, a 5-$HT_{2A}$ antagonist, a 5-$HT_{2A}$ inverse agonist, etc.), a melatonin agonist, an ion channel modulator (e.g., blocker), a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug, and an antipsychotic agent, e.g., an atypical antipsychotic agent, in free or pharmaceutically acceptable salt form. In such methods, the therapeutic agents may be adjunctive to the compounds of the invention. As used herein the term "adjunctive" refers to any treatment that is used in conjunction with another to increase the chance of cure, or to increase the first treatment's efficacy. In other words, adjunctive therapy acts as an aid to the primary treatment. The combinations of the invention can include mixtures of the combined drugs, as well as two or more separate compositions of the drugs, which individual compositions can be, for example, co-administered together to a patient at the same of different times.

The antidepressant useful for the invention may be selected from amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenelzine sulfate, protiptyline, sertraline, tranylcypromine, trazodone, trimipramine, and velafaxine, in free or pharmaceutically acceptable salt form. In certain embodiment, the antidepressant(s) is a selective serotonin reuptake inhibitor (SSRI). In a further embodiment, the SSRI compound is selected from the group consisting of citalopram, escitalopram oxalate, fluoxetine, fluvoxamine maleate, paroxetine, sertraline, and dapoxetine, in free or pharmaceutically acceptable salt form.

The dosages of a compound of Formula I and/or the antidepressant of Method I can be the same as or lower than the approved dosage for the drug, the clinical or literature test dosage or the dosage used for the drug as a monotherapy. For example the daily dosage of compound of Formula I to be administered in combination with an antidepressant is about 1 mg to about 140 mg, in another embodiment about 1 mg to about 100 mg, in another embodiment about 10 mg to about 100 mg, in another embodiment about 10 mg to about 50 mg, in another embodiment about 10 mg to about 40 mg, in another embodiment about 20 mg to about 40 mg and in another embodiment about 1 mg to about 10 mg. The amount of antidepressant to be administered in combination with the compound of Formula I is about 0.01 mg to about 2000 mg, in another embodiment about 0.1 mg to about 200 mg, in another embodiment about 10 mg to about 200 mg. In particular embodiments, the additional therapeutic agent, e.g., the antidepressant SSRI is sertraline and the daily dosage of sertraline is between about 20 mg and 100 mg.

In a specific embodiment, the dosages of a compound of Formula I and/or the second therapeutic agents are lower than when used in a monotherapy. Therefore, in a particular embodiment, the daily dosage of a compound of Formula I is lower than 100 mg once daily, or less than 50 mg, or less than 40 mg, or less than 30 mg, or less than 20 mg, or less than 10 mg. In another preferred embodiment, the dosages of both the Compound of Formula I and the antidepressant agent are lower than the dosages used for the individual drug as a monotherapy. Therefore, in a particular embodiment, for example, Method I comprises administering (1) a Compound of Formula I at a dosage lower than 100 mg once daily, preferably less than 50 mg, more preferably less than 40 mg, still more preferably less than 30 mg, still more preferably less than 20 mg, still more preferably less than 10 mg; and (2) antidepressant, for example a SSRI such as sertaline, at a daily dosage of less than 50 mg, more preferably, less than 20 mg, still more preferably, less than 10 mg, most preferably less than 6 mg, in free or pharmaceutically acceptable salt form.

The term "GABA" refers to gamma-aminobutyric acid. The GABA compounds are compounds which bind to the GABA receptor, and include, but are not limited to one or more of doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals) or estazolam.

5$HT_{2A}$ antagonists include ketanserin, risperidone, eplivanserin, volinanserin (Sanofi-Aventis, France), pruvanserin, pimavanserin (ACP-103), MDL 100907 (Sanofi-Aventis, France), HY10275 (Eli Lilly), APD125 (Arena Pharmaceuticals, San Diego, CA), AVE8488 (Sanofi-Aventis, France) and pizotifen.

5$HT_{1A}$ agonists include repinotan, sarizotan, eptapirone, buspirone and MN-305 (MediciNova, San Diego, CA).

Melatonin agonists include melatonin, ramelteon (ROZEREM®, Takeda Pharmaceuticals, Japan), VEC-162 (Vanda Pharmaceuticals, Rockville, MD), PD-6735 (Phase II Discovery and agomelatine.

Ion channel blockers such as lamotrigine, gabapentin or pregabalin.

Orexin receptor antagonists include orexin, a 1,3-biarylurea, SB-334867-a (GlaxoSmithKline, UK), GW649868 (GlaxoSmithKline) and a benzamide derivative, for example.

Serotonin-2 antagonist/reuptake inhibitors (SARI) include Org 50081 (Organon—Netherlands), ritanserin, nefazodone, serzone and trazodone.

Neurokinin-1 drugs include Casopitant (GlaxoSmithKline).

Specific examples of additional therapeutic agents useful for the current invention include modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, zolpidem, gabaxadol, vigabatrin, tiagabine, EVT 201 (Evotec Pharmaceuticals), estazolam, ketanserin, risperidone, eplivanserin, volinanserin (Sanofi-Aventis, France), pruvanserin, pimavanserin (ACP-103), pizotifen, MDL 100907 (Sanofi-Aventis, France), HY10275 (Eli Lilly), APD125 (Arena Pharmaceuticals, San Diego, CA), AVE8488 (Sanofi-Aventis, France), repinotan, sarizotan, eptapirone, buspirone, MN-305 (MediciNova, San Diego, CA), melatonin, ramelteon (ROZEREM®, Takeda Pharmaceuticals, Japan), VEC-162 (Vanda Pharmaceuticals, Rockville, MD), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon—Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, velafaxine, chlorpromazine, haloperidol, droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone, ziprasidone and paliperidone, asenapine, lurasidone, iloperidone and cariprazine, in free or pharmaceutically acceptable salt form.

The compounds of Formula I and their pharmaceutically acceptable salts and salt crystals may be made using the methods as described and exemplified in any of the following patents or applications: U.S. Pat. Nos. 6,548,493; 7,238,690; 6,552,017; 6,713,471; RE39,680; RE39,679; PCT/US08/03340; U.S. application Ser. No. 10/786,935; WO 2009/114181 and WO 2011/133224, the contents of each of which are incorporated by reference in their entirety. If not commercially available, starting materials for these processes may be made by procedures, which are selected from the chemical art using techniques which are similar or analogous to the synthesis of known compounds. All references cited herein are hereby incorporated in their entirety by reference.

The words "treatment" and "treating" are to be understood accordingly as embracing prophylaxis and treatment or amelioration of symptoms of disease and/or treatment of the cause of the disease. In particular embodiment, the word "treatment" and "treating" refers to prophylaxis or amelioration of symptoms of the disease.

The term "patient" may include a human or non-human patient.

The term "dementia" is intended to refer to a condition or disorder characterized by the loss of cognitive ability affecting memory, thinking, language, judgment and behavior. Early symptoms of dementia may include difficulty performing tasks that require some thought (balancing a checkbook, playing games (such as bridge); learning new information; getting lost on familiar routes; having language difficulties (difficulties in finding name of familiar objects); losing interest in things previously enjoy; losing social skills. More severe symptoms of dementia include change in sleep patterns, often waking up at night; difficulty performing basic tasks such as brushing teeth or preparing a meal; forgetting details about current events; having hallucinations, violent behavior, delusions, depression, agitation; difficulty reading or writing; having poor judgment or loss of ability to recognize danger; losing the ability to recognize family members or understand language. The term "dementia" refers to any of the dementing illnesses as described herein regardless of etiology and therefore shall include but not limited to mild or severe cognition impairment and dementing illnesses such as senile dementia, Alzheimer's disease, Pick's disease, frontotemporal dementia, parasupranculear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, corticobasal degenerations, and prion disease. In a particular embodiment, dementia refers to mild cognitive impairment. In another embodiment, dementia refers to Alzheimer's disease.

The term "disorder associated with dementia" means common co-morbid psychiatric disorders or conditions associated with dementia, which include but not limited to (1) behavioral or mood disorders such as agitation/irritation, aggressive/assaultive behavior, anger, physical or emotional outbursts; (2) psychosis; (3) depression; and (4) sleep disorders. In particular embodiment of the invention, the disorders associated with dementia are disorders associated Alzheimer's disease.

The term "mild cognitive impairment" or "mild cognition impairment" (MCI, also known as incipient dementia, or isolated memory impairment) is cognitive impairment beyond that expected based on the age and education of the individual, but which is not significant enough to interfere with their daily activities. Symptoms of MCI include difficulty performing more than one task at a time, solving problems or making decisions, forgetting recent events or conversations and taking longer to perform more difficult mental activities.

If not otherwise specified or clear from context, the following terms herein have the following meanings:

a. "Alkyl" as used herein is a saturated or unsaturated hydrocarbon moiety, e.g., one to twenty-one carbon atoms in length, which may be linear or branched (e.g., n-butyl or tert-butyl), preferably linear, unless otherwise specified. For example, "$C_{1-21}$ alkyl" denotes alkyl having 1 to 21 carbon atoms. In one embodiment, alkyl is optionally substituted with one or more hydroxy or $C_{1-22}$alkoxy (e.g., ethoxy) groups. In another embodiment, alkyl contains 1 to 21 carbon atoms, preferably straight chain and optionally saturated or unsaturated, for example $R_1$ is an alkyl chain containing 1 to 21 carbon atoms, preferably 6-15 carbon atoms, 16-21 carbon atoms, e.g., so that together with the —C(O)— to which it attaches, e.g., when cleaved from the compound of Formula I, forms the residue of a natural or unnatural, saturated or unsaturated fatty acid.

Compounds of the Invention refer to Compounds of Formula I, which include any of formulae 1.1-1.18, in free, salt or prodrug form. For example, where the compounds contain acidic substituents, in base addition salt form or where the compounds contain a basic substituent, in acid addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included. Pharmaceutically acceptable salts include, for example, the hydrochloride and tosylate salts. Where dosage amounts of salts are given by weight, e.g., milligrams per day or milligrams per unit dose, the dosage amount of the salt is given as the weight of the corresponding free base, unless otherwise indicated.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. For example, wherein Y of the compound of Formula I is —C(H)($OR_1$), and $R_1$ is —C(O)—$C_{1-21}$alkyl, e.g., —C(O)—$C_3$alkyl or —C(O)—$C_9$alkyl, these compounds may hydrolyze under physiological condition to yield a compound of Formula I wherein Y is —C(H)(OH) on the one hand and $C_{1-21}$alkyl-C(O)OH, e.g., $C_3$alkyl-C(O)OH or $C_9$alkyl-C(O)OH on the other hand. As will be appreciated the term thus embraces conventional pharmaceutical prodrug forms. Wherein a prodrug (e.g., the compound of formula (I) wherein $R_1$ is —C(O)—$C_{1-21}$alkyl) is used, the dosage amount is calculated based on the amount of the compound of formula (I) wherein Y is C(═O) in free base form.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration.

The phrase "disorder(s) associated with Alzheimer's disease" includes, but is not limited to (1) behavioral or mood disorders such as agitation/irritation, aggressive/assaultive behavior, anger, physical or emotional outbursts; (2) psychosis; (3) depression; and (4) sleep disorders in patients suffering from Alzheimer's disease.

Dosages employed in practicing the present invention will of course vary depending, e.g. on the particular disease or condition to be treated, the particular Compound of the Invention used, the mode of administration, and the therapy desired. Unless otherwise indicated, an amount of the Compound of the Invention for administration (whether administered as a free base or as a salt form) refers to or is based on the amount of the Compound of the Invention in free base form (i.e., the calculation of the amount is based on the free base amount). Wherein a prodrug (e.g., the compound of formula (I) wherein $R_1$ is —C(O)—$C_{1-21}$alkyl) is used, the dosage amount is calculated based on the amount of the compound of formula (I) wherein Y is C(═O) in free base form. Compounds of the Invention may be administered by any suitable route, including orally, intra-muscularly, subcutaneously, parenterally or transdermally, but are preferably administered orally. Compounds of the Invention may be administered by any suitable route, including orally, parenterally or transdermally, but are preferably administered orally.

In general, satisfactory results for Method I and any of formulae 2.1-2.23 for the treatment or prophylaxis of various disorders associated with dementia such as a combination of at least behavioral disorders such as aggressive/assaultive behavior, anger, physical or emotional outbursts; sleep disorders; mood disorders such as agitation/irritation; depression; and/or psychosis in a patient suffering from dementia, particularly Alzheimer's disease, as set forth above are indicated to be obtained on oral administration at dosages of the order from about 1 mg to 100 mg to 140 mg once or more than once daily, preferably 2.5 mg-60 mg, e.g., 2.5 mg, 5 mg, 10 mg, 20 mg, 30 mg, 40 mg, 50 mg or 60 mg, once daily of the compound of Formula I or any of formulae 1.1-1.18 in free, pharmaceutically acceptable salt or prodrug form, preferably via oral administration. Satisfactory results for Method I and any of formulae 2.1-2.24 for the treatment of sleep disorders and/or behavioral or mood disorders alone such as aggressive/assaultive behavior, anger, physical, emotional outbursts or agitation/irritation in patients with dementia, particularly Alzheimer's disease (e.g., patients without symptoms of psychosis) are indicated to be obtained on oral administration at dosages of the order from about 1-10 mg, e.g., 2.5 mg-5 mg, e.g., 2.5 mg, 3 mg, 4 mg, 5 mg or 10 mg, of a Compound of Formula I or any of formulae 1.1-1.18, in free, pharmaceutically acceptable salt or prodrug form, once daily, preferably via oral administration.

For combination therapy, one skilled in the art can design a combination based on the level of severity (staging) of and/or the symptoms manifested in dementia, particularly Alzheimer's disease to enhance efficacy with reduce side effects. Wherein the symptoms/disorders to be treated are behavioral/mood disorders such as aggressive/assaultive behavior, anger, physical or emotional outbursts and/or agitation/irritation; or sleep disorders, but the patients do not have psychosis, the compound of the invention may be administered at a lower dosage, e.g., about 1-10 mg, e.g., 2.5 mg-5 mg, e.g., 2.5 mg, 3 mg, 4 mg, 5 mg or 10 mg, of a Compound of Formula I or any of formulae 1.1-1.18, in free, pharmaceutically acceptable salt or prodrug form, once or more than once daily, preferably via oral administration. Wherein the symptoms/disorders to be treated are psychosis as well as behavioral/mood disorders such as aggressive/assaultive behavior, anger, physical or emotional outbursts and/or agitation/irritation; or sleep disorders, the compounds of the invention may be administered at a higher dosage, e.g., about 1 mg to 100 mg to 140 mg once daily, preferably 2.5 mg-60 mg, e.g., 20 mg-60 mg, 20 mg-40 mg, e.g., 2.5 mg, 5 mg, 10 mg, 20 mg, 30 mg, 40 mg, 50 mg or 60 mg, once or more than once daily, for example, greater than 20 mg per day, preferably via oral administration.

Dosages of the second or further therapeutic agent(s) useful for the prophylaxis or treatment of dementia, particularly for the prophylaxis or treatment of Alzheimer's disease or symptoms thereof, e.g., cholinesterase inhibitor, e.g., acetylcholinesterase inhibitor or NMDA receptor antagonist can vary in range known to a person skilled in the art. The dosages can range from about 1 mg to 100 mg. In particular embodiments, the compound of the Invention may be combined with the second or further therapeutic agent(s) useful for the prophylaxis or treatment of dementia, particularly Alzheimer's disease or symptoms thereof as follows:

i) about 5 mg, 10 mg or 23 mg dosage of donepezil, in free or pharmaceutically acceptable salt form; and/or
ii) about 1.5 mg, 2 mg, 3 mg, 4.5 mg, 4.6 mg, 6 mg or 9.5 mg of rivastigmine, in free or pharmaceutically acceptable salt form; and/or
iii) about 4 mg, 8 mg, 12 mg, 16 mg or 24 mg of galantamine, in free or pharmaceutically acceptable salt form; and/or
iv) about 2 mg, 5 mg, 7 mg, 10 mg, 14 mg, 21 mg or 28 mg of memantine, in free or pharmaceutically acceptable salt form;

in combination with the Compound of the Invention as hereinbefore described, in free, pharmaceutically acceptable salt or prodrug form.

For the avoidance of doubt, any disclosure of a numerical range, e.g., "up to X" amount is intended to include the upper numerical limit X. Therefore, a disclosure of "up to 60 mg" is intended to include 60 mg.

Pharmaceutical compositions comprising compounds of the Invention may be prepared using conventional diluents or excipients and techniques known in the galenic art. Thus oral dosage forms may include tablets, capsules, solutions, suspensions and the like.

Example 1: Effect of Compound A on Reversal of Social Isolation Resulted from Repeated Stress Mice are tested for social isolation behavior after repeated exposure (once daily for 10 days) to an aggressive resident intruder mouse in the social defeat/resident intruder paradigm as describe by Berton et al., *Science* (2006) 311:864-868, the contents of which are incorporated by reference. Mice are then dosed chronically, once daily for 30 d, with either vehicle (5% DMSO/5% Tween-20/15% PEG400/75% water, 6.7 ml/kg volume) or Compound A (1 mg/kg, ip) in vehicle solution. On the day after the last drug or vehicle treatment, the mice are placed in the open field in the presence of a resident intruder mouse and the animal's behavior recorded by videotape for 10 min. The videotapes are then scored for the total time each mouse spent during a 10 min period in specified open-field quadrants. The total time (sec) spent by mice representing each drug treatment group in the Interaction Zone in proximity to the resident intruder mouse or, in the Corner Zones, at a distance from the intruder mouse is expressed as a mean (±SEM).

Results: Decreased social function is a core feature of the 'negative' symptoms of schizophrenia that are poorly addressed by existing antipsychotic medications. The social defeat/resident intruder model can be used to measure social isolation behavior in rodents. Isolation behavior has been shown to be reversed using this model, after chronic administration of anti-depressant medications with potent SERT activity, including fluoxetine (Berton et al., *Science* (2006) 311:864-868). Neither acute administration of anti-depressant medications or chronic treatment with anti-anxiety medications, like chlordiazepoxide, are similarly effective in this paradigm (Berton et. al., *Science* (2006) 311:864-868). Thus, the model has been proposed for the identification of compounds to address social isolation behavior, such as social isolation behavior resulted from repeated stress. This assay is therefore used to demonstrate reversal of social isolation behavior.

In the experiment described or similarly described above, mice are subjected to exposure to an aggressive resident intruder mouse in the social defeat/resident intruder paradigm as described in Berton et al., *Science* (2006) 311:864-868. They are then dosed chronically, once daily for 30 d, with either vehicle or Compound A (1 mg/kg, IP) in vehicle. On the day after the last drug or vehicle treatment the mice are placed in the open field in the presence of a resident intruder mouse and the total time each mouse spent during a 10 min period in defined open-field quadrants in close proximity to the intruder or in isolation to the intruder is measured. As anticipated, exposure to the aggressor mouse significantly reduced the amount of time resident mice spent in proximity to the intruder ($p<0.0.05$ compared with vehicle). However, mice treated with Compound A following exposure to the intruder paradigm, showed no significant reduction in time spent in proximity to the intruder (NS, compared with Compound A alone). Compound A treatment alone did not result in differences in time spent in the Interaction Zone, compared with untreated control mice. The data indicate that chronic treatment with Compound A results in a reversal of social defeat behavior comparable to that seen after chronic treatment with anti-depressant medications such as fluoxetine. This experiment shows that Compound A is effective in reversing social isolation resulted from repeated stress. This experiment also shows that Compound A has functional anti-depressant activity.

What We claim is:

1. A method for the treatment of cognitive impairments and/or memory impairments associated with dementia, wherein the dementia is selected from mild cognition impairment, senile dementia, Alzheimer's disease, Pick's disease, frontotemporal dementia, dementia with Lewy bodies, and vascular dementia, wherein the patient suffers from a co-morbid disorder selected from psychosis and depression, comprising administering to a patient in need thereof, a therapeutically effective amount of a compound of Formula I:

Formula I

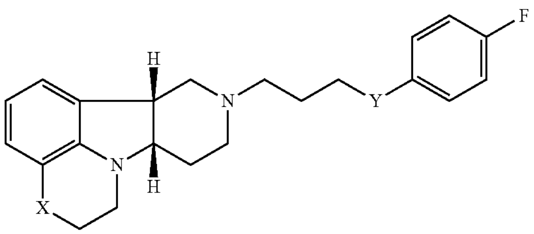

wherein:

X is $—N(CH_3)—$; and

Y is $—C(═O)$;

in tosylate salt form.

2. The method according to claim 1, wherein the dementia is Alzheimer's disease.

3. The method according to claim 1, wherein the dementia is mild cognition impairment.

4. The method according to claim 1, wherein the co-morbid disorder is psychosis.

5. The method according to claim 1, wherein the co-morbid disorder is depression.

6. The method according to claim 1, wherein the dosage of the Compound of Formula I in tosylate salt form is about 10-100 mg, measured as the amount of equivalent free base form.

7. The method according to claim 1, wherein the method treats cognitive impairments.

8. The method according to claim 1, wherein the method treats memory impairments.

9. The method according to claim 6, wherein the dosage of the Compound of Formula I in tosylate salt form is about 1-10 mg, measured as the amount of equivalent free base form.

10. The method according to claim 1, wherein the method is effective in alleviating cognitive impairment or improving cognition.

11. The method according to claim 1, wherein the method is effective in alleviating memory impairment or improving memory.

12. The method according to claim 1, wherein the dementia is selected from mild cognition impairment, senile dementia, Alzheimer's disease, and frontotemporal dementia.

13. The method according to claim 1, wherein the dementia is selected from mild cognition impairment, Alzheimer's disease, and frontotemporal dementia.

* * * * *